(12) United States Patent
Gawalt (10) Patent No.: US 8,465,808 B2
(45) Date of Patent: Jun. 18, 2013

(54) PROCESS FOR DEPOSITING AN ORGANIC ACID ON THE SURFACE OF A METAL COMPOSITION

(75) Inventor: Ellen S. Gawalt, Pittsburgh, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 1076 days.

(21) Appl. No.: 11/542,742

(22) Filed: Oct. 4, 2006

(65) Prior Publication Data

US 2007/0077440 A1   Apr. 5, 2007

Related U.S. Application Data

(60) Provisional application No. 60/723,729, filed on Oct. 5, 2005.

(51) Int. Cl.
*B05D 7/14* (2006.01)
*B05D 1/02* (2006.01)

(52) U.S. Cl.
CPC .... *B05D 7/14* (2013.01); *B05D 1/02* (2013.01)
USPC ........................................ 427/409; 427/421.1

(58) Field of Classification Search
CPC .................................. B05D 7/14; B05D 1/02
USPC .............................................. 427/409, 421.1
See application file for complete search history.

(56) References Cited

U.S. PATENT DOCUMENTS

| | | | |
|---|---|---|---|
| 5,776,748 A * | 7/1998 | Singhvi et al. ................ | 435/180 |
| 6,146,767 A * | 11/2000 | Schwartz ...................... | 428/457 |
| 6,368,338 B1 * | 4/2002 | Konya et al. .................. | 606/200 |
| 6,635,269 B1 * | 10/2003 | Jennissen ...................... | 424/423 |
| 7,517,546 B2 * | 4/2009 | Hofer et al. ................... | 427/2.11 |

FOREIGN PATENT DOCUMENTS

WO   WO 02/20873 A2 *   3/2002

OTHER PUBLICATIONS

Shustak et al., "Preparation and Characterization of n-Alkanoic Acid Self-Assembled Monolayers Adsorbed on 316L Stainless Steel," Langmuir 2004, 20, 7499-7506.*
Folkers et al., "Self-Assembled Monolayers of Long-Chain Hydroxamic Acids on the Native Oxides of Metals," Langmuir 1995, 11, 813-824.*
Yee et al., "Self-Assembled Monolayers of Alkanesulfonic and -phosphonic Acids on Amorphous Iron Oxide Nanoparticles," Langmuir 1999, 15, 7111-7115.*
Colin A. Scotchford et al., Growth of Human Osteoblast-Like Cells on Alkanethiol on Gold Self-Assembled Monolayers; The Effect of Surface Chemistry, 1998 John Wiley & Sons, Inc., J Biomed Mater Res. 41, 431-442, 1998.
Elaine Cooper et al., The Effect of Alkyl Chain Length and Terminal Group Chemistry on the Attachment and Growth of Murine 3T3 Fibroblasts and Primary Human Osteoblasts on Self-Assembled Monolayers of Alkanethiols on Gold, J. Mater. Chem., 2000, 10, 133-139.
Galit Shustak et al., Preparation and Characterization of n-Alkanoic Acid Self-Assembled Monolayers Adsorbed on 316L Stainless Steel, Langmuir 2004, 20, 7499-7506, American Chemical Society.

* cited by examiner

*Primary Examiner* — William Phillip Fletcher, III
(74) *Attorney, Agent, or Firm* — Buchanan Ingersoll & Rooney PC; Craig G. Cochenour (57) ABSTRACT

A process for modifying a surface of a metal is provided. The process includes providing a metal surface having a metal oxide, contacting the metal oxide with an organic acid having a hydroxamic acid, a sulphonic acid, or a carboxylic acid functional group, and depositing the organic acid on the surface of the metal oxide for providing a modified metal surface. Modified metal compositions are disclosed having a metal surface or a metal alloy surface having a metal oxide, and an organic acid having a functional group that is deposited onto the surface of the metal oxide forming a self assembled monolayer, multiple monolayers, or a film of a sulphonate, a hydroxamic acid, or a carboxylate with —COOH, —OH and —$NH_2$ terminal tail groups on the native oxide surface of the metal or the metal alloy.

4 Claims, 5 Drawing Sheets

PROCESS FOR DEPOSITING AN ORGANIC ACID ON THE SURFACE OF A METAL COMPOSITION

BENEFIT OF PRIOR PROVISIONAL PATENT APPLICATION

This utility patent application claims the benefit of co-pending U.S. Provisional Patent Application Ser. No. 60/723,729, filed Oct. 5, 2006, entitled "Modified Metal Oxides And A Process For Making The Same", having the same named applicant as inventor, namely, Ellen S. Gawalt. The entire contents of U.S. Provisional Patent Application Ser. No. 60/723,729 is incorporated by reference into this utility patent application.

BACKGROUND OF THE INVENTION

1. Field of the Invention

Modified metal oxides are provided. The modified metal oxides of this invention may be used as biomaterials that have surfaces that are resistant to cell adhesion. Processes to prepare the modified metal oxides of this invention are also disclosed.

2. Description of the Background Art

Inhibiting the non-specific adhesion of cells and proteins to biomaterials such as stents, catheters and guide wires is an important interfacial issue that needs to be addressed in order to reduce the surface related implant complications. Medical grade stainless steel 316L has been widely used as a biomaterial due to its corrosion resistance and very good mechanical properties. It is employed in many medical devices such as guide wires, orthopedic implants, and most commonly in the manufacture of vascular stents. Stents are used after angioplasty, a surgical method to clear the narrowing of the arteries, to prevent the re-closure of the artery. Though, this process is very successful, some complications arise due to thrombosis and neointima formation on the stents because like most artificial materials, stainless steel 316L provides a good surface for non-specific protein and cell adhesion. Therefore, interfacial modification to render the surface "inert" to attachment of proteins and cells is necessary. It is known that surface chemistry that prevents the protein and cell adhesion to the substrates, minimizes the host-implant (animal or human) inflammatory responses and prevents non-specific adhesion of proteins to render the substrate inert. However, research on surface modifications to stainless steel 316L used as a biomaterial is sparse. The present invention is a significant step towards mitigating cell adhesion by formation of monolayers with functionalized tail groups on 316L substrate.

In the past two decades, self assembled monolayers (SAMs) have developed as a commonly employed method to alter the interfacial properties of the material for their potential applications in the field of adhesion, corrosion inhibition, nano-lubricants and nano-scale devices. One of the most significant advantages of SAMs over other methods of surface coating is the ease in engineering interfacial structures at the molecular level and the ability to tailor the surface properties by functionalizing the terminal group of the SAMs. The model systems for SAMs have been thiols on gold and silanes on silicon.

Others have proposed oligoethylene glycol (OEG) terminated thiols on gold substrates as the model to render a surface inert to cellular and protein adhesion. There have been proposed that there are four characteristics of an inert surface: (1) the surface has to be polar, (2) has hydrogen bond acceptor groups, (3) no hydrogen bond donor groups, and (4) overall charge of the surface must be neutral. Inertness is a general property of a group of surfaces and not a specific property of OEG terminated SAMs, which are the model substrates for cell and protein resistance. According to this theory, hydrophobic surfaces are adsorbing. Others have proposed that more proteins adhere on hydrophobic surfaces due to hydrophobic effect by which proteins are expelled from the aqueous solution in order to increase hydrogen bonding among water molecules at the expense of less favorable water-protein interactions. Expelled proteins readily displace water from the hydrophobic surface region and get adsorbed.

Cooper et al. found that 3T3 fibroblasts and primary human osteoblasts attachment and spreading on methyl-terminated thiols on gold were poor compared to carboxylic acid terminated SAMs. Cooper et al. also found that the chain length affected the cell attachment only in case of methyl terminated thiols and not on hydroxyl and carboxylic acid terminated SAMs. Similar results were found using osteoblast cell lines where the focal contact and cell growth was highest for COOH terminated SAMs and least on methyl terminated thiols on gold. Using silane based self assembly, there have been several works on silicon which specify that hydrophobic substrates resist protein and cell adhesion more compared to controls and hydrophilic surfaces. It is believed that the cell adhesion on organically modified surfaces is a function of many parameters including but not limited to substrate, tail functionality, hydrophilicity and conformation of the monolayer on the substrate.

Although there is a large body of work performed on model substrates such as gold and silicon, these substrates cannot be employed in biomedical applications due to their poor mechanical properties and standard thiol chemistry has not been successfully employed on native SS316L and other oxides. Additionally, experiments, which utilized gold coated and uncoated stainless steel stents in patients with coronary artery disease, showed an increased risk of restenosis after placement of gold-coated stents in patients vs. uncoated stents. It is noteworthy that though stainless steel 316L is widely used as a biomaterial, the surface has been pretreated to remove the oxide layer.

Shustak et al. (Langmuir 2004, 20(18): pages 7499-7506) observed bidentate bonding on the electrochemically induced dodecanoic acid SAMs adsorbed on 316L stainless steel substrates, which were modified by fast electrochemical deposition of the acid by applied electrical potential.

In spite of this background art, there remains a very real and substantial need for a modified metal oxide, and more specifically a modified metal oxide that may be used as a biomaterial that is resistant to surface cell adhesion, and a process for making the modified metal oxide.

SUMMARY OF THE INVENTION

The present invention has met the above-described need. The modified metal oxides of the present invention preferably comprise a metal oxide having a surface comprising a self assembled monolayer of an alkylphosphonate, a carboxylate, a hydroxamic acid, or sulfonate. More specifically, the modified metal oxides of this invention preferably comprise a native metal oxide having a covalently bound, mechanically stable, ordered monolayer of phosphonic, carboxylic, hydroxamic or sulfonic acids with varying tail groups on the native oxide surface.

The present invention provides a modified metal composition comprising a metal surface having a metal oxide, and an organic acid having a phosphonic acid, a hydroxamic acid, a carboxylic acid, or sulfonic acid functional group that is deposited onto the metal oxide surface. Preferably, the modified metal oxide surface of this invention, as described herein, includes wherein the phosphonic acid has a formula $PO_3H_2C_nH_{2n}X$, and wherein the carboxylic acid has a formula $CO_2HC_nH_{2n}X$, and wherein the sulphonic acid has a formula $SO_3HC_nH_{2n}X$, and wherein the hydroxamic acid has a formula XCONHOH, wherein X is selected from the group consisting of $CH_3$, COOH, OH, $NH_2$, and Br, and wherein n is a number ranging from greater than about 4 to less than or equal to about 30, and wherein n is a number more preferably greater than or equal to about 8 and less than or equal to about 20. In one preferred embodiment of this invention, the modified metal oxide surface as described herein, includes wherein the organic acid is a self assembled monolayer deposited onto the metal oxide surface. In another embodiment of this invention as described herein, the modified metal surface of the present invention includes wherein the organic acid is a film deposited onto the surface of the metal oxide.

In a more preferred embodiment of this invention as described herein, the modified metal oxide surface is stainless steel.

In another embodiment of this invention as described herein, the modified metal oxide surface includes wherein the metal comprises about 51 percent by weight nickel oxide and about 49 percent by weight titanium oxide.

Another embodiment of this invention as described herein provides wherein the metal is an element of the Periodic Table of The Elements (IUPAC) that forms positive ions when its compounds are in solution and whose oxides form hydroxides rather than acids with water. Geologically, metals usually occur in the form of compounds that must be physically or chemically processed to yield the pure metal; common methods are application of heat, carbon reduction, electrolysis, and reduction with aluminum or magnesium. Examples of metals include but are not limited to the following elements: iron, nickel, titanium, chromium, manganese, molybdenum, cooper, aluminum, copper, zirconium, and tantalum.

Other embodiments of this invention provide the modified metal as described herein wherein the metal is an alloy. For example, but not limited to, the alloy may contain two or more of the following: nickel, molybdenum, titanium, silicon, copper, aluminum, chromium, manganese, zirconium, tantalum, and iron, and combinations thereof.

In a preferred embodiment of this invention, the modified metal oxide surface includes wherein the organic acid is a phosphonic acid that is selected from the group consisting of octadecylphosphonic acid (ODPA), octylphosphonic acid, tetraphosphonic acid, 16-hydroxyhexadecanephosphonic acid, 11-hydroxyundecane phosphonic acid, 12-carboxydodecanephosphonic acid, and 4-carboxytetraphosphonic acid.

In a preferred embodiment of this invention, the modified metal surface includes wherein the organic acid is a carboxylic acid that is selected from the group consisting of stearic acid (n-octadecanoic acid), octylcarboxylic acid, 16-hydroxyhexadecanoic acid, 1,12-dodecandioic acid, 12-aminododecanoic acid, and 12-bromododecanoic acid.

In a preferred embodiment of this invention, the modified metal surface includes wherein the organic acid is a sulphonic acid. For example, but not limited to, the sulphonic acid is octadecylsulphonic acid.

Another embodiment of this invention provides a process for modifying a surface of a metal comprising providing a metal having a metal oxide surface, contacting the metal oxide surface with an organic acid having a phosphonic acid, a hydroxamic acid, sulphonic acid, or a carboxylic acid functional group, and depositing the organic acid having the functional group on the surface of the metal oxide for providing a modified metal oxide surface. This process includes wherein the phosphonic acid has a formula $PO_3H_2C_nH_{2n}X$ and wherein the carboxylic acid has a formula $CO_2HC_nH_{2n}X$, and wherein the sulphonic acid has the formula $SO_3HC_nH_{2n}X$, and wherein the hydroxamic acid has a formula XCONHOH, wherein X is selected from the group consisting of $CH_3$, COOH, OH, $NH_2$, and Br, and n is a number that ranges from greater than about 4 to about less than or equal to 30, and preferably n is a number from about greater than or equal to 8 to about 20. This process includes wherein the organic acid is deposited onto the surface of said metal oxide as a self assembled monolayer or as a film having a thickness from about 20 Angstroms to about 100 Angstroms, and preferably from about 20 Angstroms to about 60 Angstroms. The metal may be as described herein, such as for example but not limited to, metal elements of the Periodic Table, stainless steel, nitinol, or a metal alloy.

In another embodiment of this invention, a medical device is provided comprising a metal oxide surface modified with an organic acid having a phosphonic acid, a hydroxamic acid, sulphonic acid, or a carboxylic acid functional group that renders the metal oxide surface resistant to cell adhesion. In a preferred embodiment of this invention, the medical device, as described herein, includes a metal oxide surface modified with an organic acid that is phosphonic acid that has a formula $PO_3H_2C_nH_{2n}X$, a carboxylic acid that has a formula $CO_2HC_nH_{2n}X$, a sulphonic acid that has a formula $SO_3HC_nH_{2n}X$, or a hydroxamic acid that has a formula XCONHOH, wherein X is selected from the group consisting of $CH_3$, COOH, OH, $NH_2$, and Br, and n is a number greater than about 4 to less than or equal to about 30, and preferably n is a number from about 8 to about 20. Preferably, the medical device includes wherein the organic acid is deposited onto the surface of the metal oxide as a self assembled monolayer or as a film. The medical device may be constructed of a metal, as described herein, such as for example but not limited to, a metal element of the Periodic Table, stainless steel, nitinol, or a metal alloy.

In another embodiment of this invention, a biomaterial is provided comprising at least one metal wherein said metal has metal oxide surface that is modified with an organic acid having a phosphonic acid, a hydroxamic acid, sulphonic acid, or a carboxylic acid functional group that renders said modified metal oxide resistant to cell adhesion. The biomaterial comprises a metal oxide surface, preferably modified with an organic acid that is phosphonic acid having a formula $PO_3H_2C_nH_{2n}X$, a carboxylic acid having a formula $CO_2HC_nH_{2n}X$, a sulphonic acid having a formula $SO_3HC_nH_{2n}X$, or a hydroxamic acid having a formula XCONHOH, wherein X is selected from the group consisting of $CH_3$, COOH, OH, $NH_2$, and Br, and n is a number greater than about 4 and less than or equal to about 30, and wherein n is preferably a number from about 8 to about 20. The biomaterial as described herein, includes wherein the organic acid is deposited onto a surface of the metal oxide as a self assembled monolayer or as a film. The metal may be such as for example but not limited to any metal element of the Periodic Table, stainless steel, nitinol, or a metal alloy. The metal alloy may be for example but not limited to a metal alloy containing at least two or more of the following: nickel, iron, tantalum, zirconium, chromium, molybdenum, silicon, manganese, titanium, and copper, and combinations thereof.

BRIEF DESCRIPTION OF THE DRAWINGS

FIG. 2.

FIG. 3.

DETAILED DESCRIPTION OF THE INVENTION

As used herein the term "biomaterial" means any biocompatible (non-toxic) material that is used to construct an artificial tissue, organ, prosthesis, and rehabilitation device, a medical appliance, or a medical tool. For example but not limited to, a biomaterial may be used in the construction of a stent used in performing cardiac angioplasty or dialysis, implantable artificial joints, plates, and other body parts, or implantable organs such as an artificial heart.

As used herein the term "animal" means any member of the animal kingdom including but not limited to animals and human beings.

As used herein the term "hydroxamic acid" is a class of chemical compounds sharing the same functional in which an amine is inserted into a carboxylic acid. The general structure for a hydroxamic acid is X—CO—NH—OH where X is an organic residue, CO is a carbonyl group, and a hydroxylamine as NH—OH. Hydroxamic acids may be synthesized from aldehydes via the Angeli-Rimini reaction known by those skilled in the art.

As used herein the term "alloy" means a solid or liquid mixture of two or more metals, or of one or more metals with one or more nonmetallic elements, such as for example but not limited to silicon. One example of an alloy is carbon steel.

The present invention provides a modified metal composition comprising a metal surface having a metal oxide, and an organic acid having a phosphonic acid, a hydroxamic acid, a sulphonic acid, or a carboxylic acid functional group that is deposited onto the metal oxide surface. Preferably, the modified metal oxide surface of this invention, as described herein, includes wherein the phosphonic acid has a formula $PO_3H_2C_nH_{2n}X$, and wherein the carboxylic acid has a formula $CO_2HC_nH_{2n}X$, and wherein the sulphonic acid has the formula $SO_3HC_nH_{2n}X$, and wherein the hydroxamic acid has a formula XCONHOH, wherein X is selected from the group consisting of $CH_3$, COOH, OH, $NH_2$, and Br, and wherein n is a number ranging from greater than about 4 to less than or equal to about 30. Preferably, n is a number from about 8 to about 20. In one preferred embodiment of this invention, the modified metal oxide surface includes wherein the organic acid is a self assembled monolayer deposited onto the metal oxide surface. In another embodiment of this invention the modified metal oxide surface includes wherein the organic acid is a film deposited onto the surface of the metal oxide. Preferably, the thickness of the deposited layer or film is from about 20 Angstroms to about 100 Angstroms, and more preferably the thickness of the deposited monolayer or film is from about 20 Angstroms to about 60 Angstroms. More preferably, the monolayer (single layer) is one molecular layer with a height of about 20 Angstroms upon the metal oxide surface, however, multiple layers may be deposited upon the metal oxide surface to achieve a thickness of about 100 Angstroms, or five monolayers wherein each monolayer has a thickness of about 20 Angstroms.

In a more preferred embodiment of this invention as described herein, the modified metal oxide surface is stainless steel.

In another embodiment of this invention as described herein, the modified metal oxide surface includes wherein the metal comprises about 51 percent by weight nickel oxide and about 49 percent by weight titanium oxide, commonly known as "memory metal", or nitinol.

In another embodiment of this invention as described herein, the modified metal is a metal element of the Periodic Table that forms positive ions when its compounds are in solution and whose oxides form hydroxides rather than acids with water.

Other embodiments of this invention provide the modified metal oxide as described herein wherein the metal is an alloy. For example, but not limited to, the alloy may contain two or more of the following: nickel, molybdenum, titanium, silicon, copper, aluminum, chromium, manganese, zirconium, tantalum, and iron, and combinations thereof.

In a preferred embodiment of this invention, the modified metal oxide surface includes wherein the organic acid is a phosphonic acid that is selected from the group consisting of octadecylphosphonic acid, octylphosphonic acid, tetraphosphonic acid, 11-hydroxyundecane phosphonic acid, 16-hydroxyhexadecane phosphonic acid, 12-carboxydodecanephosphonic acid, and 4-carboxytetraphosphonic acid.

In a preferred embodiment of this invention, the modified metal oxide surface includes wherein the organic acid is a carboxylic acid that is selected from the group consisting of stearic acid (n-octadecanoic acid), octylcarboxylic acid, 16-hydroxyhexadecanoic acid, 1,12-dodecandioic acid, 12-aminododecanoic acid, and 12-bromododecanoic acid.

Another embodiment of this invention provides a process for modifying a surface of a metal comprising providing a metal oxide surface, contacting the metal oxide surface with an organic acid having a phosphonic acid, a hydroxamic acid, a sulphonic acid, or a carboxylic acid functional group, and depositing the organic acid having the functional group on the surface of the metal oxide for providing a modified metal oxide surface. This process includes wherein the phosphonic acid has a formula $PO_3H_2C_nH_{2n}X$ and wherein the carboxylic acid has a formula $CO_2HC_nH_{2n}X$, and wherein the sulphonic acid has the formula $SO_3HC_nH_{2n}X$, and wherein the hydroxamic acid has a formula XCONHOH, wherein X is selected from the group consisting of $CH_3$, COOH, OH, $NH_2$, and Br, and n is a number ranging from greater than about 4 to about 30, and preferably n is a number from about 8 to about 20. This process preferably includes wherein the organic acid is deposited onto the surface of said metal oxide as a self assembled monolayer or as a film. The metal may be as described herein, such as for example but not limited to, any metal element of the Periodic Table, stainless steel, nitinol, or a metal alloy.

In another embodiment of this invention, a medical device is provided comprising a metal oxide surface modified with an organic acid having a phosphonic acid, a hydroxamic acid, a sulphonic acid, or a carboxylic acid functional group that renders the metal oxide surface resistant to cell adhesion. In a preferred embodiment of this invention, the medical device, as described herein, includes a metal oxide surface modified with an organic acid that is phosphonic acid that has a formula $PO_3H_2C_nH_{2n}X$, a carboxylic acid that has a formula $CO_2HC_nH_{2n}X$, a sulphonic acid that has the formula $SO_3HC_nH_{2n}X$, or a hydroxamic acid that has a formula XCONHOH, wherein X is selected from the group consisting of $CH_3$, COOH, OH, $NH_2$, and Br, and n is a number ranging from greater than about 4 to less than or equal to about 30, and preferably n is a number from about 8 to about 20. Preferably, the medical device includes wherein the organic acid is deposited onto the surface of the metal oxide as a self assembled monolayer or as a film. The medical device may be constructed of a metal, such as for example but not limited to, any metal element of the Periodic Table, stainless steel, nitinol, or a metal alloy, as described herein.

In another embodiment of this invention, a biomaterial is provided comprising at least one metal wherein said metal has a metal oxide surface that is modified with an organic acid having a phosphonic acid, a hydroxamic acid, a sulphonic acid, or a carboxylic acid functional group that renders said modified metal oxide resistant to cell adhesion. The biomaterial comprises a metal oxide surface, preferably modified with an organic acid that is phosphonic acid having a formula $PO_3H_2C_nH_{2n}X$, a carboxylic acid having a formula $CO_2HC_nH_{2n}X$, a sulphonic acid that has the formula $SO_3HC_nH_{2n}X$, or a hydroxamic acid having a formula XCONHOH, wherein X is selected from the group consisting of $CH_3$, COOH, OH, $NH_2$, and Br, and n is a number ranging from about greater than 4 to about less than or equal to 30, and preferably n is a number from about 8 to about 20. The biomaterial as described herein, includes wherein the organic acid is deposited onto a surface of the metal oxide as a self assembled monolayer or as a film. The metal may be such as for example but not limited to a metal element, stainless steel, nitinol, or a metal alloy. The metal alloy may be for example but not limited an alloy containing at least two or more of the following: nickel, iron, tantalum, zirconium, chromium, molybdenum, silicon, manganese, titanium, and copper, and combinations thereof.

EXAMPLES

The following examples demonstrate the instant invention in greater detail. These examples are not intended to limit the scope of the invention in any way.

To control the implant surface, we developed a novel method of self-assembly of long chain acids on stainless steel 316L. Self assembled monolayers of long chain carboxylic and phosphonic acids with —COOH, —OH and —$NH_2$ terminal tail groups were formed on the native oxide surface of medical grade stainless steel 316L. The strong covalent attachment and uniformity of the film on the substrate was confirmed using diffuse reflectance infrared spectroscopy, atomic force microscopy, and contact angle analysis. Cell adhesion experiments were conducted using 3T3 fibroblast cells to investigate the effect of changing the tail group at the interface and the head group that binds to the substrate on the adhesion of cells. Cell adhesion was reduced by about 80% using methyl terminated SAMs when compared to the control stainless steel 316L. Hydrophilic tail groups presented at the interface did not reduce cell adhesion significantly. The methyl terminated SAMs of phosphonic and carboxylic acid on stainless steel substrates form films that are substantially "inert" or resistant to cell adhesion.

Materials and Methods:
Materials:

SS316L (stainless steel 316L) substrate was obtained from Goodfellow Inc. and was 99.99% pure. THF, methanol, stearic acid (98+%), 16-hydroxyhexadecanoic acid (98%), 12-aminododecanoic acid (95%) and 1,12-dodecanedicarboxylic acid (99%) were obtained from Aldrich Chemical Co. Octadecylphosphonic acid was obtained from Alfa Aesar. All chemicals were used without any further purification. 12-carboxydodecanephosphonic acid and 11-hydroxyundecanephosphonic acid were synthesized in the lab using the literature procedures known by those skilled in the art.

Substrate Preparation:

Stainless steel 316L substrates were cut into 1 cm×1 cm coupons and polished using the Buehler Ecomet 4 mechanical polisher using 220, 400, 800, 1200 grids silicon carbide paper followed by a 1 μm diamond suspension. The polished samples were cleaned by ultra-sonication in methanol (about 15 minutes) followed by immersion in boiling methanol to remove traces or residues of organics and metallic dust. The cleaned substrates were stored in the oven at 120° C. (centigrade).

Monolayer Formation:

SAMs of octadecylphosphonic acid (ODPA) was prepared by dipping the cleaned substrates in 1 mM solution of the acid in dry THF and removing the excess solution by evacuation (0.1 Torr). Functionalized phosphonic acid (12-carboxydodecanephosphonic acid (C12COOH—P), 11-hydroxyundecanephosphonic acid (C11OH—P) SAMs were prepared by the same method but were stored in the oven at 120° C. for a minimum of about 2 hours before analysis.

SAMs of long chain carboxylic acids with varying functional groups at the tail (octadecylcarboxylic acid (ODCA), 12-aminododecanecarboxylic acid (C12NH$_2$), 16-hydroxyhexadecanoic acid (C16OH) and 1,12-dodecanedicarboxylic acid (C12COOH)) were prepared as follows: The cleaned substrates were placed in an ice bath for 1 hr and then dipped in warm (50° C.) THF solution of the respective acid for 2 hours and stored in oven at 120° C. overnight before further analysis.

Substrate Analysis:
Diffuse Reflectance Infrared Fourier Transform (DRIFT) Spectroscopy Nexus 470 FT-IR, a Diffuse Reflectance Infrared Fourier Transform spectroscopy (DRIFT); purchased from Thermo Electron Corporation was used to analyze the ordering and orientation of the molecule in the monolayer formed. 1024 scans with a resolution of 1 cm$^{-1}$ were performed on each sample and ratioed with a background reference spectra collected of a cleaned stainless steel substrate. The spectra were collected under nitrogen flow. The samples were rinsed, sonicated in THF (distilled tetrahydrofuran) and analyzed by DRIFT spectroscopy again to test the chemical and mechanical stability of the mono layers.

Contact Angle Goniometry

Static contact angles were measured using VCA Optima Goniometry to determine the wettability of the surface. Measurements were made using the procedure described by Bain et al. (J. Am. Chem. Soc. 1989; Vol. 111, pgs. 321-335), known by those skilled in the art. About 1 μl drop of deionized water (purified with a Millipore Milli Q plus system) was formed at the end of the micro-liter syringe and brought into contact with the surface. Average contact angle value±standard deviation of 6 readings each on at least 3 samples have been reported.

Atomic Force Microscopy

Atomic force microscope operating in non-contact mode using PicoSPM (Molecular Imaging Corp.) was used to confirm the uniformity of the film on the surface. AFM imaging (topography and phase) of the ODCA and ODPA modified substrates were performed in non-contact mode at ambient conditions. The cantilevers (non-contact mode cantilevers from Molecular Imaging Corp.) were silicon nitride cantilever with a resonance frequency around 160-170 kHz and a typical spring constant of around 40 N/m. The roughness analysis on the 2D topography image was based on calculation of standard deviation of all height values within the given imaged area (rms roughness).

Cell Experiments

For cell experiments, 3T3 Swiss Albino embryo fibroblast cells of mouse were obtained from ATCC (CCL-92). The cells were grown in Dulbecco's modified Eagle medium (DMEM, Invitrogen Corp.) supplemented with 10% calf serum, 1% penicillin/Streptavidin antibiotic. The cells were passaged every 3 days and were discarded after 15 passages. Cells were removed from the T 75 flasks by trypsinization, washed once with DMEM, suspended in culture medium. The modified SS316L substrates were placed in a 24 well plate and were sterilized with 70% ethanol for 10 mins and then rinsed with sterile distilled water 3 times. The sterilized substrates were left in the hood to dry. The suspended 3T3 Swiss Albino embryo fibroblast cells were then counted with a Haemocytometer after staining them with trypan blue and seeded at the density of 10,000 cells/well into each of the wells containing the substrates modified with respective acids After incubating the cells in humidified air with 5% $CO_2$ for 24 hours at 37° C., the samples were rinsed with PBS three times and analyzed for live dead cells. Viability/cytotoxicity kit (L-3224) obtained from Molecular Probes was used to provide a simultaneous determination of live and dead cells. The assay contains Calcein AM and ethidium homodimer dyes. The live cells are identified by the enzymatic conversion of the non-fluorescent cell permeant calcein AM to intensely fluorescent calcein. This calcein is retained in the live cells and produces a green fluorescence. Ethidium homodimer is excluded by the intact plasma membrane of live cells but enters cells with damaged membranes (dead cells), binds to nucleic acid and produces a bright red fluorescence. Live cells are in green and dead cells in red when viewed under fluorescent microscope.

After washing with PBS, 0.5 ml of the live/dead stain was added to each well and the well plate was covered with aluminum foil and placed in the incubator for about 30 minutes. Three samples of each type of modification were used for every set and four such sets were performed. Each sample was mounted on the microscope slide and viewed under fluorescence Nikon Eclipse microscope at 10× magnification. Five different spots were observed and counted for cells on each sample and average value used for calculation of significance. Viability calculations were performed on each sample by counting the number of live cells in the total number of cells.

Statistical Methods

ANOVA was used to determine the statistical difference between the means of data sets for cell experiments with the modified substrates and multiple comparisons of the sample means was performed using Bonferroni post test using confidence level of 0.05.

Results and Discussion:

DRIFT Spectroscopy

SAMs of carboxylic, sulphonic, and phosphonic acid with varying terminal groups were formed on stainless steel 316L (SS316L) substrates using the solution deposition technique discussed herein. SAMs of functionalized phosphonic acids were prepared by dipping clean substrates into 1 mM solution of the respective acids and storing them in the oven at 120° C. Functionalized SAMs of carboxylic acid was formed by dipping the cold substrates in warm (50° C.) solution of respective acid in THF (distilled). Dry THF was used for the deposition method because it is known by those skilled in the art that water competes with the alkanoic acid for binding sites. The modified SS316L were analyzed by DRIFT spectroscopy. On the basis of extensive study, it has been observed that an 'ordered' film is characterized by alkyl chains in an all-trans configuration that are all tilted from the normal to the surface at the same angle (30° in case of thiols on gold) with the $v_{CH2\ asymm}$ less than 2918 $cm^{-1}$.

Figure 1:
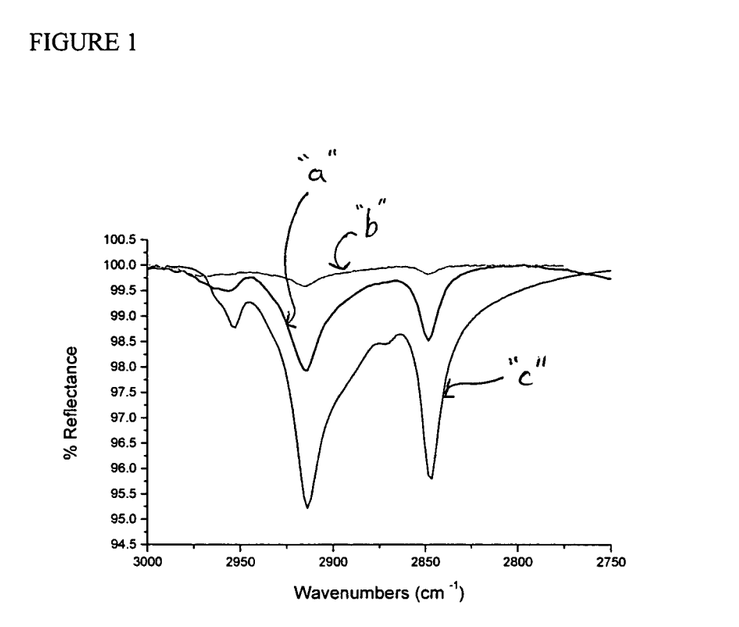
FIG. 1 shows a DRIFT spectra of stearic acid on SS316L (deposition indicated by reference letter "a", rinse indicated by reference letter "b", and tape test indicated by reference letter "c").

In the present invention, all the acids formed a well-ordered monolayer as indicated by the DRIFT $v_{CH2\ asymm}$ values. The monolayers formed readily and were not removed after rinsing with THF. The samples were then sonicated in THF. The $v_{CH2\ asymm}$ using DRIFT was found to be less than 2918 $cm^{-1}$ after both rinse and sonication tests indicating that the monolayers formed were strongly bound to the surface. Formation of strong covalently bound, ordered monolayers of octadecylphosphonic acid on SS316L were observed. Sample IR spectra of stearic acid SAMs on SS316L can be seen in FIG. 1 and values for the examples of the molecules used to form the monolayers of this invention are set forth in Table 1.

Figure 2:
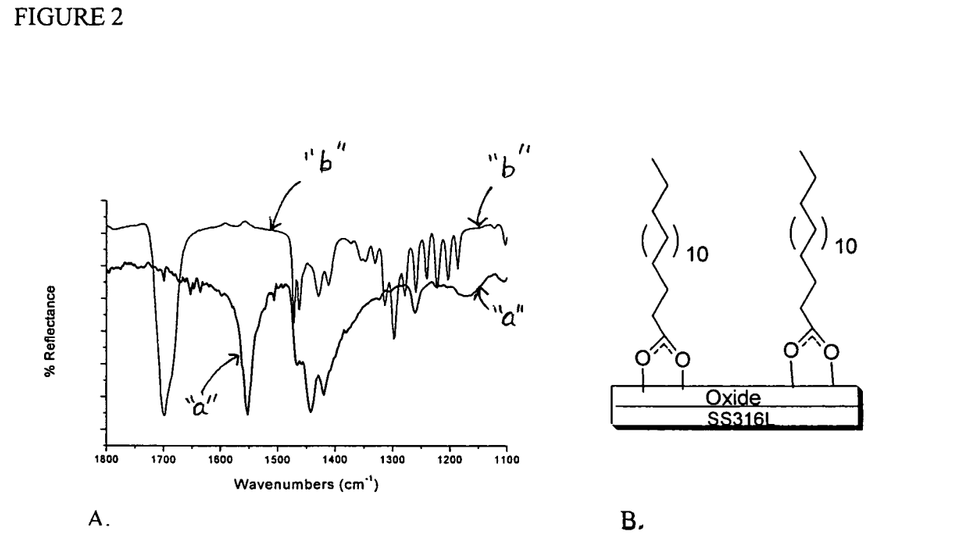
FIG. 2A shows C—O region of stearic acid deposited on stainless steel (indicated by reference letter "a") and solid (indicated by reference letter "b")
FIG. 2B shows surface bonding of ODCA on stainless steel 316L.

The interaction or bonding mode of the head groups (carboxylic and phosphonic acid) varies among surfaces and the interaction appears to be monodentate, bidentate or tridentate for phosphonic acid on different substrates and to be monodentate (unsymmetrical carboxyl configuration) or bidentate for carboxylic acid. Changes in the C—O region of the spectra for SAMs with carboxylic acid head group indicate a chemical transformation of the head group. In the bulk material there are peaks at 1690 $cm^{-1}$, 1465 $cm^{-1}$ which are representative of $v_{C=O}$, $v_{C-O}$ IR stretches. After deposition, there is only a peak for carboxylate $v_{COO^-\ sym}$ and $vCOO^-_{asymm}$ stretches at 1551 $cm^{-1}$ and 1446 $cm^{-1}$. $v_{C=O}$ peak at around 1700 $cm^{-1}$ is not present. This indicates that the acid groups have become carboxylate groups and thus, the monomers are bound to the surface in a bidentate fashion (FIG. 2). This bonding persists even after the rinse and adhesion test described earlier. Since some head groups were entrapped in the interface as carboxylic acids and so they observed some C=O peaks too. Without being bound by theory, we believe that the process of the instant invention of solution deposition leads to a bidentate bonding without any excess acid at the interface. The P—O of phosphonic acid head group was found to be bidentately bonded to the stainless steel substrate as observed by IR stretches and confirmed by XPS data.

Contact Angle Analysis

Contact angle data was collected to determine the relative wettability of the modified substrates because surface wettability may play an important role in facilitating cell adhesion and has been shown to be a useful marker for estimating the monolayer quality. Densely packed and well-ordered SAMs predominantly expose methyl groups at the surface, decreasing the surface wettability. In contrast, loosely packed SAMs expose a substantial fraction of methylene groups in addition to methyl groups at the surface, increasing the wettability and decreasing the contact angle. On the other hand, if the tail terminus of the SAMs is hydrophilic, the resulting contact angle values will be relatively more hydrophilic than the control sample under consideration.

Octadecylcarboxylic acid gave a contact angle value of 104° (one hundred and four degrees) with water compared to a contact angle of 45° for the control stainless steel substrate. This is consistent with the values found in literature for hydrophobic methyl terminated thiols on gold and silanes on silicon. The hydrophilic tail terminated SAMs like 1, 12 dodecane dicarboxylic acid, 12 amino dodecanoic acid and 16-hydroxy hexadecanoic acid (Table 2) had lower contact angle values than the control SS316L substrate. ($CH_3$ terminated SAMs=108±0.7, OH terminated SAMs=31.9±3.6, COOH terminated SAM=47±2.4, gold surface=75.8±1.9)

TABLE 1

IR stretch values for monolayers of various acids on SS316L.

| Acid used in monolayer formation | Notation | $\nu_{CH2\,symm}$ Deposition (cm$^{-1}$) | $\nu_{CH2\,asymm}$ Deposition (cm$^{-1}$) | $\nu_{CH2\,symm}$ Rinsed (cm$^{-1}$) | $\nu_{CH2\,asymm}$ Rinsed (cm$^{-1}$) |
|---|---|---|---|---|---|
| Octadecyl phosphonic acid | ODPA | 2912 | 2846 | 2912 | 2846 |
| Octadecyl carboxylic acid | ODCA | 2914 | 2847 | 2916 | 2847 |
| 11-Hydroxy undecane phos. acid | C11OH—P | 2913 | 2846 | 2914 | 2846 |
| 12-carboxy dodecane phos. acid | C12COOH—P | 2914 | 2847 | 2915 | 2848 |
| 16-hydroxy hexadecane phos. acid | C16OH—C | 2917 | 2848 | 2916 | 2849 |
| 1,12-dodecane dicarboxylic acid | C12COOH—C | 2913 | 2849 | 2913 | 2849 |
| 12-amino dodecanoic acid | C12NH2—C | 2918 | 2848 | 2918 | 2849 |

TABLE 2

Contact Angle Values

| Acid used in monolayer formation | Contact angle values | Standard deviation |
|---|---|---|
| Control SS316L | 53.6° | 3.0° |
| ODPA | 108° | 3.0° |
| ODCA | 104.1° | 0.5° |
| C12COOH—P | 52.3° | 1.8° |
| C11OH—P | 59.8° | 4.2° |
| C14COOH—C | 42° | 5.7° |
| C16OH—C | 48.6° | 2.7° |
| C12NH$_2$—C | 38.4° | 7.5° |

Table 2 shows the average contact angle measurements with water for at least three samples with six values on each sample. The values were found to be hydrophobic for interface with methyl terminus and were relatively more hydrophilic for the —OH, —COOH and —NH$_2$ terminated SAMs compared to control SS316L substrate. The standard deviation of NH$_2$ and COOH terminated SAMs was found to be higher than others as it is difficult to disrupt the interchain hydrogen bonding of the tail terminus.

AFM (Atomic Force Microscopy) Imaging

Figure 3A:
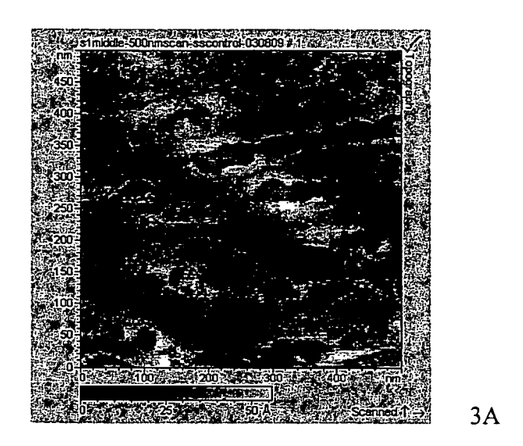
FIG. 3A shows an AFM image of control SS316L, and FIG. 3B SS316L modified oxide surface with ODCA.
Figure 3B:
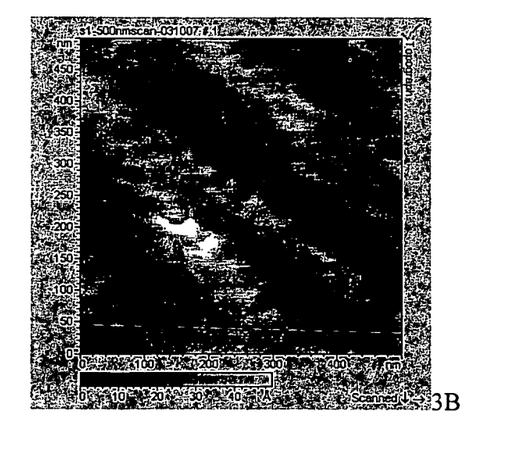
Figure 4:
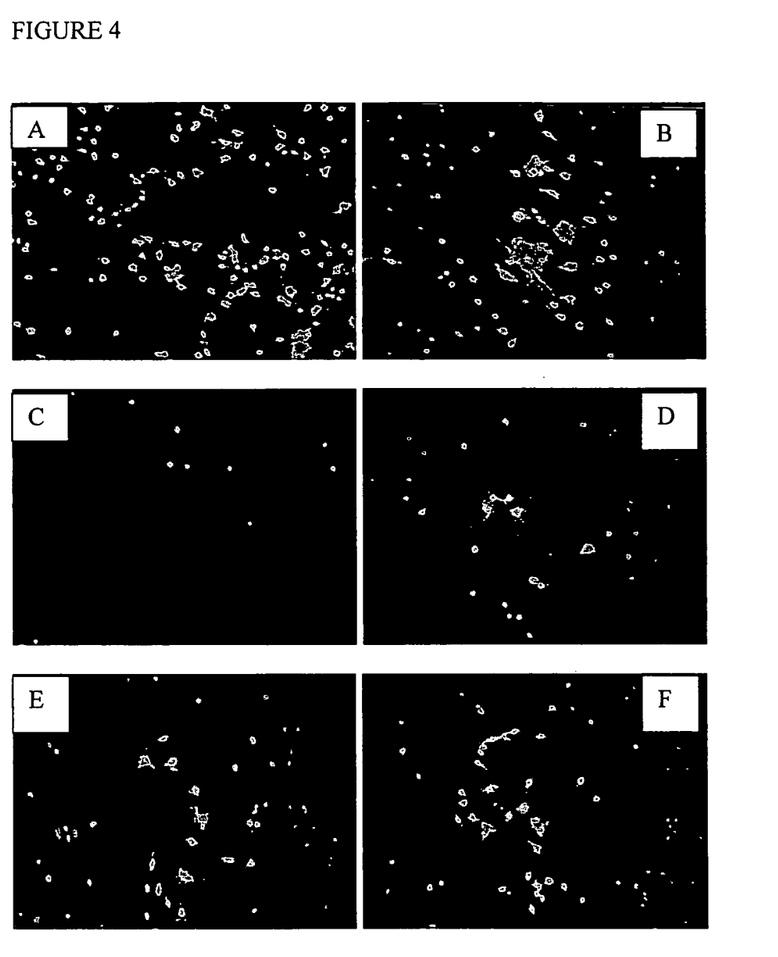
FIG. 4 shows Live/dead images of (A) Control, (B) amine terminated carboxylic acid, (C) methyl terminated phosphonic acid, (D) methyl terminated carboxylic acid, (E) carboxy terminated carboxylic acid, and (F) hydroxy terminated carboxylic acid. Magnification 10× objective. The percentage viability was calculated by dividing the number of live cells by the total number of cells.

The coverage on the surface by the organic monolayer was determined by performing a topography scan of the substrate using AFM. FIG. 4 shows a 500 nm scan of bare polished stainless steel 316L substrate and octadecylcarboxylic acid modified substrate. The roughness analysis on the 2D topography image was based on calculation of standard deviation of all height values within the given imaged area (rms roughness). The rms roughness value of control SS316L substrate before reaction with ODCA was 11 Å (eleven angstroms), and after reaction with ODCA it was 10 Å. This indicates that a single monolayer of molecules covers the oxide surface. There was no evidence of micelle or island formation visible in the film (FIG. 3)

Cell Experiments

In order to determine the stability of the interfacial systems developed in this work under physiological conditions and their viability for use in biomedical devices (and more specifically medically implantable devices), cell adhesion studies using fibroblasts were conducted on four sets of independent experiments with three samples each of all functionalized SAM with carboxylate and phosphonate head groups. The substrates were modified with —CH$_3$, —COOH, —OH terminated phosphonic acids and —CH$_3$, —OH, —COOH and —NH$_2$ terminated carboxylic acids by the solution deposition process of the present invention as set forth herein. Cells were seeded at the density of 10,000 cells/well and incubated for about 24 hours. The samples were then rinsed with PBS three times and analyzed for live dead cells using the Viability/cytotoxicity kit. In the live-dead images, the live cells are represented by green while the dead ones are in red. As can be seen in figure, the numbers of dead cells are very few when compared to the live ones indicating that the viability is high. The viability on the control SS316L substrate and all the modified substrates were greater than 96%, except for C18P and C12OH—P that had a slightly lower viability of about 92%.

The number of live and dead cells attached to the modified SS316L was evaluated by fluorescence microscopy for the presence and shape of the cells on each surface. FIG. 4 shows that the number of live cells attached to the amine terminus is close to that in the control. Additionally, the cells looked uniformly and densely well spread on amine terminated samples and control samples. The number of cells on the methyl terminated phosphonic acid (4c) is the least in number followed by methyl terminated carboxylic acid (4d). The cells on methyl terminated SAMs (ODPA and ODCA) were rounded and small indicating a poor interaction with the surface.

Figure 5:
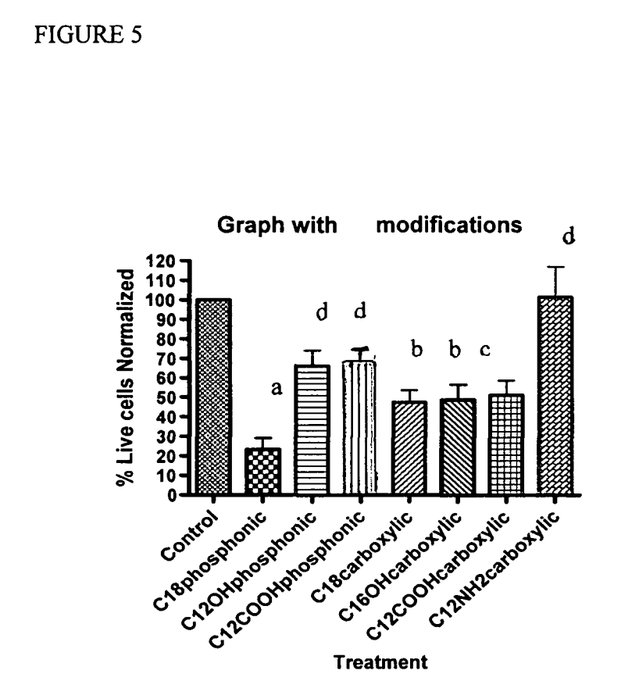
FIG. 5 shows normalized number of 3T3 cells on each modified SS316L substrate after 24 hours. a=$p<0.001$ compared to the control SS316L, b=$p<0.01$ compared to control SS316L, c=$p<0.05$ compared to control SS316L, d=$p>0.05$ compared to control SS316L.

Statistical analysis of the number of cells attached to the surface was performed by one-way ANOVA. FIG. 5 shows the normalized number of cells on each of the modified substrates along with their statistical significance of difference compared with control SS316L. Independent experiments were normalized to the control set at 100% to enable comparison between different experiments.

There was a significant difference between control and C18P ($p<0.001$), control and C18C ($p<0.01$), control and C12COOH ($p<0.05$), control and C16OH ($p<0.01$), while the number of cells attached to C12OH—P, C12COOH—P and C12NH$_2$ terminated SAMs were not significantly different from the control ($p>0.05$) using a one-way ANOVA followed by Bonferroni post hoc test (known by those skilled in the art).

The number of cells attached to the methyl terminated SAMs were the least in number ($p<0.01$). This is due to the hydrophobic nature of the tail functionality. This finding is analogous to a number of previous studies that have shown that hydrophobic methyl terminated thiols on gold induce minimal cell adhesion and spreading of fibroblast cells. However, this finding is in contrast to the computational and experimental studies that found that hydrophilic surfaces resisted cell adhesion best. Here, amine terminated SAMs supported the highest density and spreading of 3T3 fibroblast. This suggest that the positively charged amine groups attract more cells. Significantly higher levels of cellular adhesion on amine terminus were attributed to the electrostatic interaction between the high density of positively charged NH$_3^+$ species on the surface and the negatively charged glycosaminoglycans and silalic acid residues on the surface of the cell membrane. Ionic head groups had higher thrombogeniety. COOH terminated SAMs contain high concentrations of fibronectin cell binding domains, which is related to enhanced cell attachment, spreading and proliferation of 3T3 mouse fibroblast cells. While CH$_3$ terminated SAMs have impaired fibronectin receptor function due to the blockage of Beta 1 integrin mobility resulting in fewer cell attachment and spreading.

In this study other hydrophilic tail groups (OH and COOH) with the phosphonic acid head group with OH and COOH terminus had more cells ($p>0.05$-but not significantly different from control) than their carboxylic acid counter part ($p<0.05$ and $p<0.01$ respectively for OH and COOH terminated SAMs) even though methyl terminated ODPA (phosphonic head) had fewer cell attachments than ODCA (carboxylic head). These results indicate that the cell adhesion to the substrate is a complex phenomenon and is a multifactoral property of not only the substrate but also head group, tail functional group, hydrophilicity, packing density and chain length of the monomer. We conclude that cell adhesion in vitro for mouse NIH 3T3 fibroblast cells on modified stainless steel is a combination of stability and hydrophilicity of the surface.

Table 3A and 3B show the results of deposition of various organic acids of this invention having a combination of different tail and head groups on metal oxide surfaces.

The term "Ordered" means that an alkyl-chain ordered film was formed on the surface of the metal oxide using the specific organic acid specified. Empty blocks appear in Tables 3A and 3B when no experiment was performed.
Procedures The procedures used to obtain the results in Tables 3A and 3B are listed below:
Phosphonic Acid Head Group:
  P1—Dip in solution (1 mM) for about 1 minute. Place in vac line.
  P2—Dip in solution (1 mM) for about 1 minute. Place in oven overnight at 120 degrees C.
Carboxylic Acid and Hydroxamic Acid Head Group:
  C1—Substrate from oven, placed in ice for about 45 minutes, dipped into warm (about 50-55 degrees C.) solution of 1 mM acid for about 2 hours. Placed in the oven overnight without meniscus.
  C2—Substrate from oven, placed in ice for 45 about minutes, dipped into warm (about 50-55 degrees C.) solution of 1 mM acid for about 2 hours. Placed in the oven overnight with meniscus.
  Dipping—Dip sample into acid solution for about 15 minutes and allow to dry in air for about 30 minutes. Analyze by IR.
  Ice—Place samples in dish on ice for about one hour. After about 45 minutes begin heating the solution to about 100° C. At the end of one hour, transfer cold samples into solution and heat for about two hours (lid on top of beaker). Allow to dry for about 30 minutes before analysis by IR.
  Cleaning of all samples—Sand metal oxide foil with 150, 320, 400 grit sand paper. Cut the iron into 1×1 cm samples. Clean samples with acetone. Put each individual sample into a test tube with methanol and sonicate for at least about 15 minutes. Pour out the methanol and refill with new methanol. Heat at about 200° C. for at least about 15 minute (methanol starts to evaporate). Pour off the methanol and allow to dry in oven for about 30 minutes. Samples can be stored in oven

TABLE 3A

X = CH$_3$; All on cleaned native oxide surfaces

| | Octadecyl sulfonic acid pKa = 2 | Octadecyl Phosphonic acid pka = 4 | Octyl phosphonic acid | Hydroxamic acid pKa = 8 | Octadecyl Carboxylic acid pKa = 10 | Heptadecyl Carboxylic acid pKa = 10 |
|---|---|---|---|---|---|---|
| SS316L | | Ordered P1 | Ordered P1 | No formation | Ordered C1 | Ordered C1 |
| Fe | Ordered dip | Ordered P1 | | Ordered ice | Ordered C2 | |

TABLE 3A-continued

X = CH₃; All on cleaned native oxide surfaces

| | Octadecyl sulfonic acid pKa = 2 | Octadecyl Phosphonic acid pka = 4 | Octyl phosphonic acid | Hydroxamic acid pKa = 8 | Octadecyl Carboxylic acid pKa = 10 | Heptadecyl Carboxylic acid pKa = 10 |
|---|---|---|---|---|---|---|
| Ni | | Ordered P1 | Ordered | Ordered | No formation | Ordered |
| Mo | | Ordered P2 | | No formation | Ordered C2 | |
| Cr | | Ordered P1 | | No formation | No formation | |
| Mn | | Ordered P1 | | Ordered 2 mM, C2 | No formation | |
| Nitinol | Ordered | Ordered | Ordered | Ordered | No formation | Ordered |
| Ti | Ordered | Ordered | Ordered | No formation | No formation | No formation |

TABLE 3B

Top Row of header = Tail Group
Bottom Row of header = Head group

| | C$_n$ | | | | |
|---|---|---|---|---|---|
| | 11 OH POOH | 12 COOH POOH | 16 OH COOH | 12 COOH COOH | 12 NH2 COOH |
| SS316L | Ordered P2 | Ordered P2 | Ordered C1 | Ordered C1 | Ordered C1 |
| Fe | | | Ordered C1 | Ordered C1 | Ordered C1 |
| Ni | Ordered | Ordered | Ordered C1 | Ordered C1 | No formation |
| Mo | | | Ordered C1 | No formation | Ordered C1 |
| Nitinol | Ordered | Ordered | Ordered | Ordered | No formation |
| Ti | Ordered | Ordered | Ordered | Ordered | No formation |

Tables 4A and 4B show the results of deposition after the procedures set forth below.

Procedures

Procedures for Results in Table 5A and 5B:

All monolayers/films were deposited using the aerosol spray method with a TLC spray and nitrogen gas stream is used for deposition method Phosphonic acids head groups-one (ODPA) and two sprays (COOH, OH—,) were used on all surfaces. Then the samples dried under vacuum (0.1 Torr) overnight.

Carboxylic acids head groups-3 sprays were used and the samples were dried in the oven (120 C.) for about 20 minutes.

Solution Acid Concentration for Each Acid is Included in the Table.

TABLE 4A

X = CH₃; All on cleaned native oxide surfaces
Empty blocks = experiment not performed

| | Octadecyl sulfonic acid pKa = 2 | Octadecyl Phosphonic acid pka = 4 | Octyl phosphonic acid | Hydroxamic acid pKa = 8 | Octadecyl Carboxylic acid pKa = 10 | Heptadecyl Carboxylic acid pKa = 10 |
|---|---|---|---|---|---|---|
| SS316L | | Ordered | Ordered | No formation | Ordered | Ordered |
| Fe | Ordered | Ordered | Ordered | Ordered | Ordered | |
| Ni | | Ordered 0.35 mM | Ordered 0.75 mM | Ordered 2 mM | No formation | Ordered 2 mM |
| Mo | | Ordered | Ordered | No formation | Ordered | |
| Cr | | Ordered | Ordered | No formation | No formation | |
| Mn | | Ordered | Ordered | Ordered | No formation | |
| Nitinol | Ordered 0.75 mM | Ordered 0.35 mM | Ordered 0.75 mM | Ordered 2 mM | No formation | Ordered 2 mM |
| Ti | | Ordered 0.35 mM | Ordered 0.75 mM | No formation | No formation | Ordered 2 mM |

TABLE 4B

Top Row of header = Tail Group
Bottom Row of heading = Head group

| | $C_n$ | | | | |
|---|---|---|---|---|---|
| | 11<br>OH<br>POOH | 12<br>COOH<br>POOH | 16<br>OH<br>COOH | 12<br>COOH<br>COOH | 12<br>NH2<br>COOH |
| SS316L | Ordered | | Ordered | Ordered | Ordered |
| Fe | Ordered | | Ordered | Ordered | Ordered |
| Ni | Ordered<br>0.75 mM | Ordered<br>0.50 mM | Ordered<br>1.5 mM | Ordered<br>1.5 mM | No<br>formation |
| Mo | Ordered | | Ordered | Ordered | Ordered |
| Cr | Ordered | | Ordered | Ordered | Ordered |
| Mn | Ordered | | Ordered | Ordered | Ordered |
| Nitinol | Ordered<br>0.75 mM | Ordered<br>0.50 mM | Ordered<br>1.5 mM | Ordered<br>1.5 mM | No<br>formation |
| Ti | Ordered<br>0.75 mM | Ordered<br>0.50 mM | | | |

These examples show that self assembled monolayers of functionalized carboxylic acids and phosphonic acids were formed on the native oxide surface of stainless steel by the solution deposition process of this invention. Cellular adhesion to hydrophobic tail terminus was found to be statistically significantly less than those for charged functionalities especially amine terminus. Carboxylate and hydroxyl terminated SAMs showed varied significance for the two acids indicating that the cell adhesion to the substrate is a complex phenomenon and is a multifactoral property of not only the substrate but also head group, tail functional group, hydrophilicity and the packing density of the monomer.

Whereas particular embodiments of this invention have been described above for purposes of illustration, it will be self evident to those persons skilled in the art that numerous variations of the details of the present invention may be made without departing from the invention as defined in the appended claims.

What is claimed is:

1. A process for modifying a surface of a metal comprising:
providing a metal surface having a metal oxide, wherein said metal is stainless steel,
contacting said metal oxide with an organic acid solution or aerosol having a combination of a concentration of from 0.35 mM to 2.0 mM and a temperature ranging from above 0° Centigrade to 120° Centigrade and having a hydroxamic acid or a carboxylic acid functional group, wherein said carboxylic acid has a formula $CO_2HC_nH_{2n}X$ or wherein said hydroxamic acid has a formula XCONHOH, and wherein X is selected from the group consisting of $CH_3$, COOH, OH, $NH_2$, and Br, and n is a number ranging from greater than about 4 to less than or equal to 30, and
depositing said organic acid having said functional group on the surface of said metal oxide by solution or spray deposition for providing a modified metal surface wherein said organic acid that is deposited on said surface of said metal oxide has a monolayer free of micelle or island formation and a thickness ranging from greater than or equal to 12 Angstroms to less than or equal to 100 Angstroms.

2. A process for modifying a surface of a metal comprising:
providing a metal surface having a metal oxide, wherein said metal is nitinol,
contacting said metal oxide with an organic acid solution or aerosol having a combination of a concentration of from 0.35 mM to 2.0 mM and a temperature ranging from above 0° Centigrade to 120° Centigrade and having a hydroxamic acid or a carboxylic acid functional group, wherein said carboxylic acid has a formula $CO_2HC_nH_{2n}X$ or wherein said hydroxamic acid has a formula XCONHOH, and wherein X is selected from the group consisting of $CH_3$, COOH, OH, $NH_2$, and Br, and n is a number ranging from greater than about 4 to less than or equal to 30, and
depositing said organic acid having said functional group on the surface of said metal oxide by solution or spray deposition for providing a modified metal surface wherein said organic acid that is deposited on said surface of said metal oxide has a monolayer free of micelle or island formation and a thickness ranging from greater than or equal to 12 Angstroms to less than or equal to 100 Angstroms.

3. A process for modifying a surface of a metal comprising:
providing a metal surface having a metal oxide, wherein said metal is a metal alloy,
contacting said metal oxide with an organic acid solution or aerosol having a combination of a concentration of from 0.35 mM to 2.0 mM and a temperature ranging from above 0° Centigrade to 120° Centigrade and having a hydroxamic acid or a carboxylic acid functional group, wherein said carboxylic acid has a formula $CO_2HC_nH_{2n}X$ or wherein said hydroxamic acid has a formula XCONHOH, and wherein X is selected from the group consisting of $CH_3$, COOH, OH, $NH_2$, and Br, and n is a number ranging from greater than about 4 to less than or equal to 30, and
depositing said organic acid having said functional group on the surface of said metal oxide by solution or spray deposition for providing a modified metal surface wherein said organic acid that is deposited on said surface of said metal oxide has a monolayer free of micelle or island formation and a thickness ranging from greater than or equal to 12 Angstroms to less than or equal to 100 Angstroms.

4. The process of claim 3 including wherein said metal alloy comprises at least two or more of the elements selected from the group consisting of iron, nickel, chromium, manganese, tantalum, silicon, titanium, copper, zirconium, and molybdenum.

* * * * *